United States Patent
Young

(10) Patent No.: US 8,888,783 B2
(45) Date of Patent: Nov. 18, 2014

(54) OSTEOTOME

(75) Inventor: Michael John Radley Young, South Devon (GB)

(73) Assignee: Orthosonics Limited (GB)

( * ) Notice: Subject to any disclaimer, the term of this patent is extended or adjusted under 35 U.S.C. 154(b) by 1609 days.

(21) Appl. No.: 11/792,198

(22) PCT Filed: Dec. 2, 2005

(86) PCT No.: PCT/GB2005/004618

§ 371 (c)(1),
(2), (4) Date: Nov. 19, 2007

(87) PCT Pub. No.: WO2006/059120

PCT Pub. Date: Jun. 8, 2006

(65) Prior Publication Data

US 2008/0188878 A1 Aug. 7, 2008

(30) Foreign Application Priority Data

Dec. 2, 2004 (GB) .................................... 0426503.9

(51) Int. Cl.
| | |
|---|---|
| A61B 17/00 | (2006.01) |
| A61B 17/14 | (2006.01) |
| A61B 17/32 | (2006.01) |
| A61B 17/16 | (2006.01) |

(52) U.S. Cl.
CPC ............. *A61B 17/16* (2013.01); *A61B 17/1664* (2013.01); *A61B 17/148* (2013.01); *A61B 17/320068* (2013.01); *A61B 2017/320072* (2013.01); *A61B 17/1642* (2013.01); *A61B 17/1637* (2013.01); *A61B 17/14* (2013.01)
USPC .............................. 606/82; 606/169; 606/177

(58) Field of Classification Search
CPC .............................................. A61B 17/320068
USPC ............................... 606/79–85, 159, 165–183
See application file for complete search history.

(56) References Cited

U.S. PATENT DOCUMENTS

| | | | |
|---|---|---|---|
| 3,680,610 A | * | 8/1972 | Lindgren ........................ 83/835 |
| 4,188,952 A | | 2/1980 | Loschilov et al. |
| 5,261,922 A | | 11/1993 | Hood |

(Continued)

FOREIGN PATENT DOCUMENTS

| | | |
|---|---|---|
| DE | 3830065 A1 | 3/1989 |
| EP | 1 380 265 A | 1/2004 |

(Continued)

OTHER PUBLICATIONS

International Search Report for International Appln. No. PCT/GB2005/004618 (PCT/ISA/210).
Ipsum—Online Patent Information and Document Inspection Service for GB2420979, www.ipo.gov.uk/p-ipsum/Case/PublicationNumber/GB2420979, printed Jun. 30, 2014.

*Primary Examiner* — Sameh Boles
(74) *Attorney, Agent, or Firm* — Carter, DeLuca, Farrell & Schmidt, LLP

(57) ABSTRACT

A tool (1, 31) for cutting bone comprises an elongate blade (7,37) connectable to a generator of longitudinal-mode ultrasonic vibrations. The blade (7,37) has two lateral cutting edges (9,10) linked by a rounded distal tip (8). A series of triangular teeth (13) extends along each cutting edge (9,10) and the distal tip (8). The blade (37) may taper towards each cutting edge (9,10) and the distal tip (8). A variant of the tool (21) comprises an elongate part-cylindrical blade (27) connectable to a generator of torsional-mode ultrasonic vibrations. The blade (27) has a cutting edge at its distal tip (28) provided with a plurality of triangular teeth (23). All forms of the tool (1, 21, 31) are particularly suitable for cutting cancellous bone around an implant to be removed during revision of a joint arthroplasty.

9 Claims, 3 Drawing Sheets

(56) References Cited

U.S. PATENT DOCUMENTS

| | | | |
|---|---|---|---|
| 5,517,889 A * | 5/1996 | Logan | 83/835 |
| 5,676,680 A | 10/1997 | Lim | |
| 5,897,570 A | 4/1999 | Palleva et al. | |
| 5,935,142 A | 8/1999 | Hood | |
| 5,935,143 A * | 8/1999 | Hood | 606/169 |
| 6,782,781 B2 * | 8/2004 | Rack | 83/13 |
| 2002/0099400 A1 | 7/2002 | Wolf et al. | |

FOREIGN PATENT DOCUMENTS

| | | |
|---|---|---|
| SU | 512761 A1 | 5/1976 |
| SU | 797675 A1 | 1/1981 |
| WO | WO 92/22259 | 12/1992 |
| WO | WO 93/01751 A | 2/1993 |

\* cited by examiner

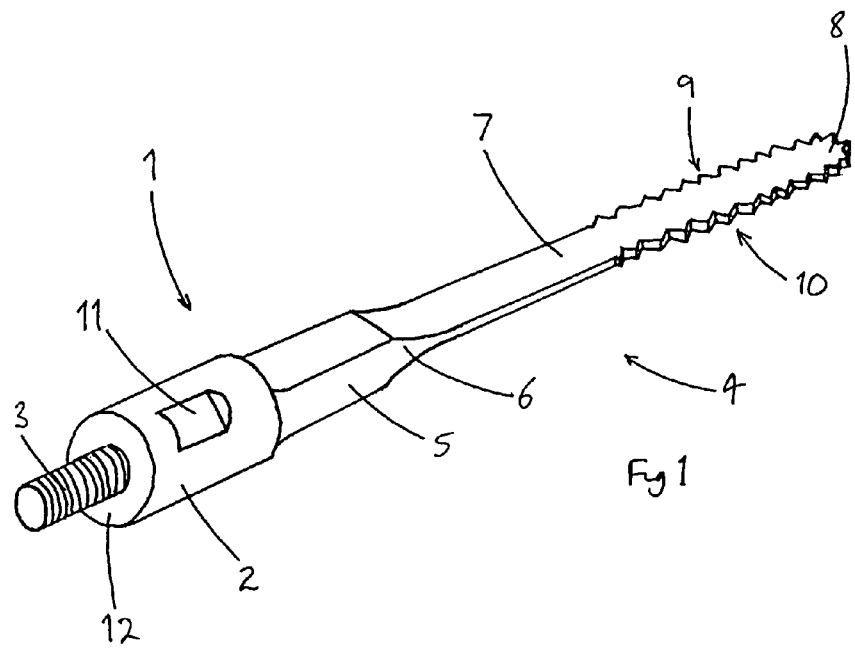
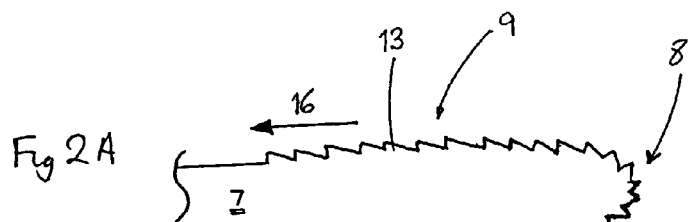
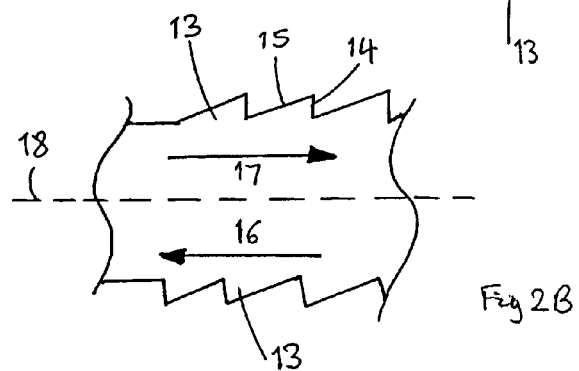

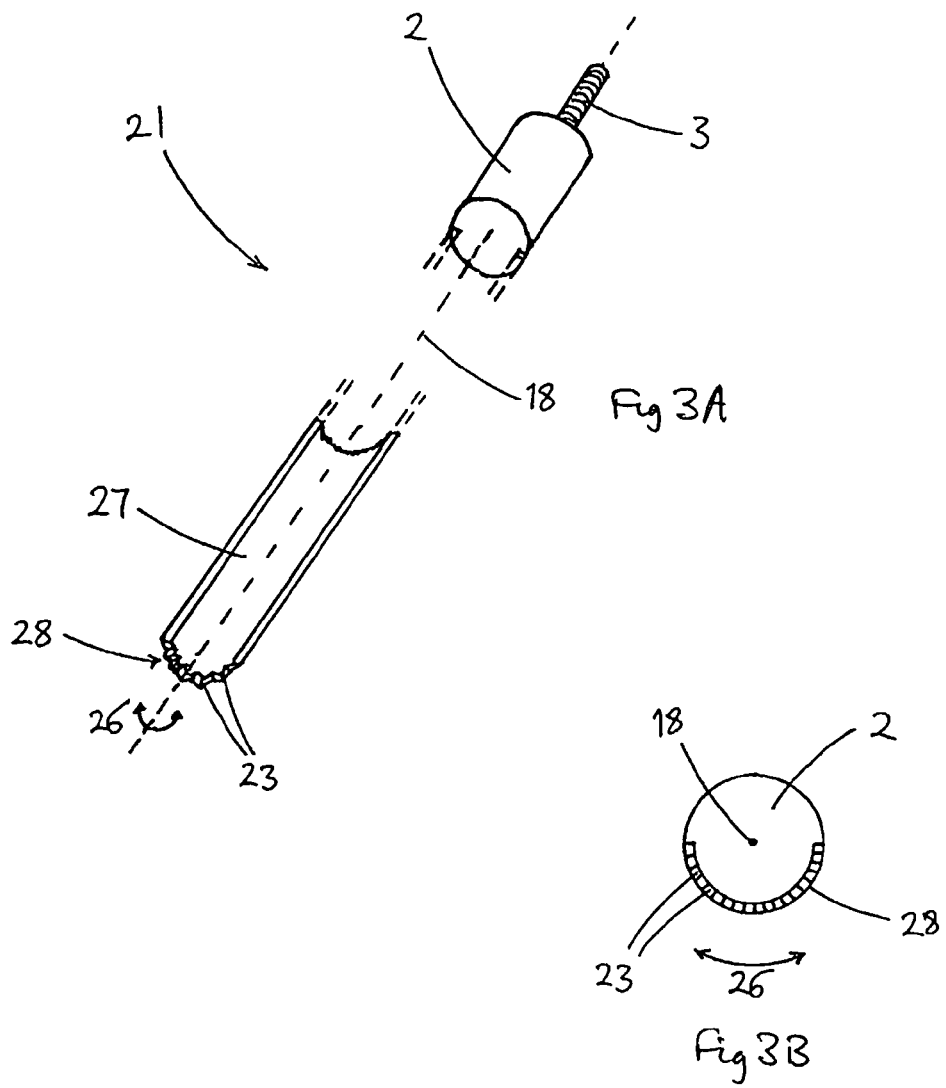

OSTEOTOME

BACKGROUND

1. Technical Field

The present disclosure relates to a tool for cutting into or through bone, for example during orthopaedic surgery. More particularly, but not exclusively, it relates to a tool for cutting through cortical or cancellous bone, for example to separate a joint prosthesis from surrounding bone as part of a revision procedure.

2. Prior Art

A frequently required procedure in orthopaedic surgery is revision of a joint arthroplasty, for example revision of a hip joint replacement, should an implanted prosthesis break or wear unacceptably over its articulating surface. The present disclosure will be described in relation to its use in hip joint revision, but is equally applicable to other joints and the terms "hip", "pelvis" and "femur" may be replaced as necessary. In many cases, an implanted prosthesis is secured in a cavity within a bone, such as a femur, using polymeric organic cement such as polymethylmethacylate. Tools have been devised to soften and remove this cement and to allow convenient removal of a worn or damaged prosthesis, followed by implantation of a replacement.

However, there has been a recent increase in the use of press-fit prostheses. No cement is used to hold these in place within the femur, pelvis, etc. Instead, the implanted portions of the prostheses have porous surfaces or surfaces coated with hydroxy-apatite, which encourage ingrowth of bone, leading to stable, well-anchored implants. This formation of cancellous bone may also occasionally occur with cement-anchored implants. While not as strong as the structural bone of the wall of the femur, the pelvis or other bone, cancellous bone is not easily susceptible to cutting using the tools devised for revising cement-anchored implants, and it has become necessary to attack cancellous bone mechanically in order to revise such implants.

Furthermore, in order to remove a prosthesis, it may be necessary to remove portions of cortical bone, which cannot be achieved without using mechanical means.

A manual osteotome is effectively a specialised form of chisel, which is forced longitudinally through the bone between a prosthesis and surrounding structural bone. The force required can be so great as to compromise the directional accuracy of the technique, and may thereby damage surrounding structural bone, especially if it is weakened by osteoporosis or the like.

Another approach is to use powered burrs to drill out the bone. These may also be difficult to guide accurately, and flexure in their elongate rotating drive shafts may lead to unacceptable collateral damage in surrounding structural bone. This approach also produces inconveniently large quantities of bone swarf, which must be removed to allow clear visualisation of the point at which the burr is cutting. Furthermore, high-speed burrs lead to significant localised frictional heating, which may also harm adjacent bone, tissue or marrow. Manual sawing through bone is a slow, tiring process, also leading to localised heating and copious bone swarf. In any case, conventional bone saws could not easily be inserted or operated between a hip or other joint prosthesis shaft and an inner wall of a femur, or between a part-spherical acetabular shell and a pelvic bone, for example.

SUMMARY

It is hence an object of the present disclosure to provide a tool for cutting bone, particularly bone adjacent an arthroplasty implant, that obviates the above disadvantages and allows accurate, rapid and convenient removal of such implants as part of a revision procedure.

According to a first aspect of the present disclosure, there is provided a tool for cutting bone comprising a means of generating ultrasonic vibrations, elongate blade means operatively connectable thereto and having at least one cutting edge provided with a plurality of serrations each having a first cutting facet substantially transverse to the direction of said ultrasonic vibrations.

In a first embodiment, the tool is adapted to be vibrated by longitudinal mode ultrasonic vibrations, for example directed substantially parallelly to a longitudinal axis of the blade means.

Preferably, the blade means then comprises an elongate substantially planar member having two substantially oppositely-facing lateral edges.

Advantageously, said lateral edges each extend substantially parallelly to the longitudinal axis of the blade means.

The elongate member may further comprise a rounded distal tip. Said distal tip may extend between a distal end of a first said lateral edge and a distal end of a second said lateral edge.

Preferably, the cutting edge extends along at least part of a respective one of said lateral edges.

Advantageously, the cutting edge extends along at least part of each said lateral edge.

The cutting edge may extend around all or part of the rounded distal tip.

A continuous cutting edge may extend around at least a distal portion of each lateral edge and the distal tip extending therebetween.

Preferably, at least part of the blade means has a cross-sectional profile tapering towards one or each lateral edge.

Advantageously, the blade means has a cross-sectional profile adjacent its distal tip tapering towards said tip.

Said tapering profile may comprise at least one angled surface located on each opposite face of the blade means.

A single angled surface may extend adjacent each lateral edge and the distal tip on each said face.

Said angled surfaces may be connected at their respective outer peripheries by an edge surface extending transversely to the general plane of the blade member.

Said edge surface may be substantially narrower than an overall thickness of the blade means.

Preferably, said tapering profile is at least coextensive with the cutting edge of the blade means.

Preferably, each serration of the or each cutting edge is generally triangular.

Each serration may have the first, cutting facet extending generally orthogonally to a local alignment of the cutting edge.

Each serration may then have a second, angled facet extending obliquely to said local alignment.

Each pair of neighbouring serrations may be so relatively aligned that a first facet of one serration of said pair is adjacent a second facet of the next serration of said pair.

Each first facet of a first lateral cutting edge may face towards a distal tip of the blade means and each first facet of a second opposite lateral cutting edge may then face towards a proximal root of the blade means.

Preferably, each serration extends outwardly from the cutting edge, substantially in the plane of the elongate member.

In a second embodiment, the tool is adapted to be vibrated by torsional mode ultrasonic vibrations.

The blade means then preferably comprises an elongate member having a curved cross-section, optionally substantially comprising an arc of a circle.

Advantageously, said cross-section is substantially constant along a whole of the elongate member.

The tool may be so adapted as to be torsionally vibratable about an longitudinal axis extending through the centre of said circle.

Preferably, a distal tip of the elongate member comprises the cutting edge of the tool.

The serrations of the cutting edge may be generally triangular.

The serrations may extend distally from the tip of the member.

A portion of the elongate member adjacent its tip may taper longitudinally towards said tip.

The tapered portion may comprise an angled surface located on a concave face of a curved elongate member.

In each embodiment, the generator means is advantageously adapted to generate ultrasonic vibrations at a frequency within the range of twenty to seventy-five kilohertz.

According to a second aspect of the present disclosure, there is provided a method of cutting bony material comprising the steps of providing a tool as described in the first aspect above, applying a cutting edge of the tool to a surface of bony material to be cut, causing the tool to vibrate at an ultrasonic frequency and drawing the cutting edge of the tool across said surface.

Preferably, the cutting edge is drawn reciprocally across said surface.

Advantageously, the bony material comprises cancellous and/or cortical bone holding an orthopaedic implant to a bone of a living body, and the method comprises the step of cutting the bone as described above until the implant is separable therefrom.

BRIEF DESCRIPTION OF THE DRAWINGS

Embodiments of the present disclosure will now be more particularly described by way of example and with reference to the accompanying drawings in which:

FIG. 1 is a perspective view of a first tool embodying the present disclosure;

FIG. 2A is a plan view of a distal portion of the tool shown in FIG. 1;

FIG. 2B is a schematic plan view of an intermediate part of the distal portion shown in FIG. 2A;

FIG. 3A is a partial perspective view of a second tool embodying the present disclosure;

FIG. 3B is an elevation of a distal end of the tool shown in FIG. 3A;

DETAILED DESCRIPTION

Figure 4:
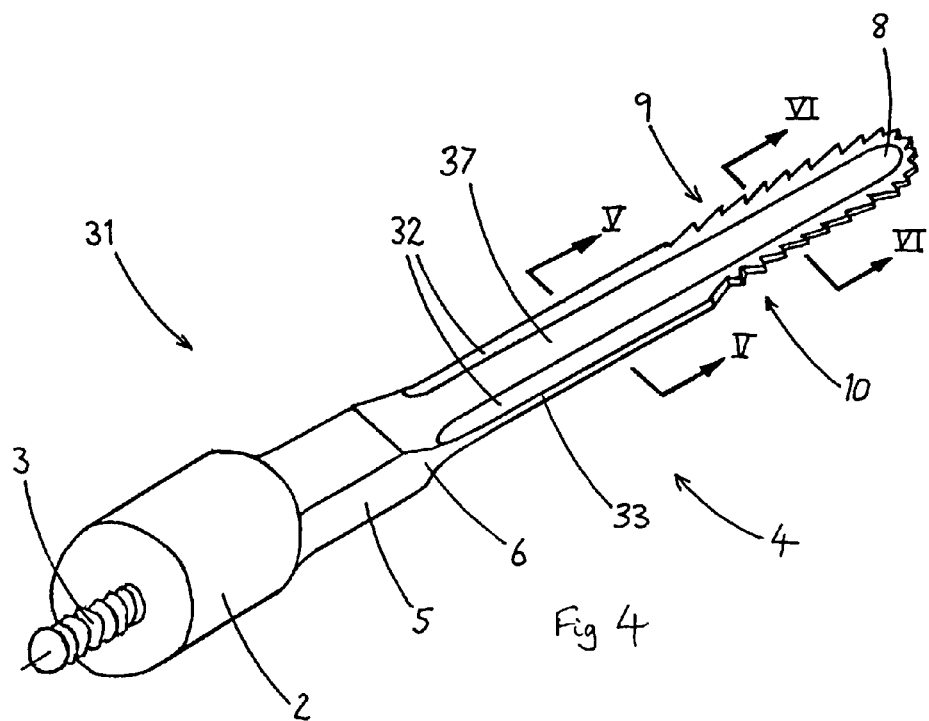
FIG. 4 is a perspective view of a third tool embodying the present disclosure.

Referring now to the Figures and to FIG. 1 in particular, a first osteotomy tool 1 comprises a cylindrical connecting body 2 provided at a proximal end with a threaded spigot 3, by which the tool 1 may detachably be connected to a generator of ultrasonic vibrations (not shown). An elongate blade portion 4 of the tool 1 extends from a distal end of the connecting body 2, and is aligned generally coaxially therewith.

The blade portion 4 comprises a proximal blade root 5 having a substantially rectangular cross-section and linked by a tapered portion 6 to a thin, flat elongate blade 7 with a generally rounded distal tip 8. A distal portion of the blade 7 has two oppositely-facing lateral cutting edges 9, 10. Each of the lateral cutting edges 9, 10 and the tip 8 is provided with a plurality of teeth 13, as shown in more detail in FIGS. 2A and 2B. A proximal portion of the blade 7 is toothless, although the relative lengths of the toothed and toothless portions may vary from that shown.

The cylindrical connecting body 2 is provided with spanner flats 11 to allow application of tightening torque sufficient to bring the tool 1 into secure contact with the ultrasound generator, allowing effective vibrational coupling through a contact surface 12 of the body 2. The tool 1 is preferably made of titanium or stainless steel.

As FIGS. 2A and 2B illustrate, the teeth 13 of the blade 7 are preferably shaped generally as conventional saw teeth, having a first edge 14 substantially orthogonal to a longitudinal axis of the blade 7 and a second edge 15 at a relatively shallow angle thereto. In a conventional saw, the first edge 14 would be sharpened, and the saw would cut when pulled (or sometimes pushed) in a longitudinal direction in which the first edge 14 is a leading edge of the tooth 13. In the present disclosure, it is believed to be unnecessary to sharpen the teeth 13.

In the tool 1 shown, the teeth 13 extend in a continuous array along a first cutting edge 9, around the tip 8 and along a second cutting edge 10, without the relative dispositions of the first and second edges 14, 15 of the teeth 13 changing. Thus, the first cutting edge 9 is adapted to cut on a longitudinal pull stroke as indicated by arrow 16 and the second cutting edge 10 is adapted to cut on a longitudinal push stroke as indicated by arrow 17.

Were the tool 1 a conventional mechanical saw, this arrangement would not be particularly effective, a push cut being particularly difficult to control in direction or force. Manual sawing at bone, even cancellous bone, produces significant frictional heating and requires considerable effort on the part of the user.

However, when the blade 7 is subjected to longitudinal mode ultrasonic vibrations, directed parallelly to the longitudinal axis 18 of the tool 1, the effectiveness of both the pull stroke 16 and the push stroke 17 is greatly improved. The velocity amplitude of the first edge 14 of each tooth 13 as it contacts the bone is much greater than the speed of the stroke 16, 17 alone. This leads to much more rapid cutting through the bone, with much less friction, and hence much less heating. The user does not need to force the tool 1 through the bone, allowing much greater accuracy and control in the cut, for both the push and pull strokes 16, 17. The tip 8 may be sunk longitudinally into the bone with only small lateral movements of the tool 1.

The tool 1 is connected to an ultrasound generator operating in the frequency range 20-75 kHz.

Thus, for a replacement hip joint prosthesis held in a cavity within a femur by friction or by interaction with cancellous bone, and requiring revision, it is relatively straightforward to sink the tool 1 between the stem of the prosthesis and the femur itself, tip first and extending generally parallelly to the stem. The tool 1 can then be moved laterally around the stem, with a gentle sawing motion, cutting through the bone and freeing the prosthesis.

Compared to the alternative approach of using powered burrs, the ultrasonically-vibrated tool 1 is significantly more accurate, and does not flex when it meets increased resistance, which might cause unacceptable collateral bone damage.

Frictional heating is lower with the tool 1 shown than with powered burrs, and the amount of bone swarf produced is significantly lower.

Manual (chisel-like) osteotomes require considerable force to drive between the prosthesis and the femur, which could damage a weakened femur wall and frequently compromises the directional accuracy of the technique.

The tool 1 may also be of use in other surgical procedures where rapid and accurate bone cutting is required, such as bone grafting or amputations.

A second osteotomy tool 21 is shown in FIG. 3A. As for the first 1, it comprises a cylindrical body 2 with a proximally-mounted threaded spigot 3 by which it is connectable to a generator of ultrasonic vibrations. However, in this case, the generator produces torsional mode ultrasonic vibrations. As for the longitudinally-vibrated first tool 1, vibrations in the frequency range 20-75 kHz are preferred.

The second tool 21 is provided with a generally hemicylindrical blade 27, aligned coaxially with the connecting body 2 along a longitudinal axis 18 of the tool 21. A distal tip 28 of the hemicylindrical blade 27 is provided with a plurality of teeth 23. The teeth 23 are shown as symmetrical, although they may be asymmetrical as for the teeth 13 of the first tool 1, set in either sense or even set in alternating senses. The tip 28 thus comprises a generally semicircular cutting edge, as shown in FIG. 3B.

The torsional mode ultrasonic vibrations transmitted through the connecting body 2 to the blade 27 thus vibrate the tip 28 as shown by arrows 26. The user rotates the second tool 21 manually about the axis 18, without needing to exert significant longitudinal force, and the ultrasonic vibrations cause the tool 21 to cut rapidly and accurately into the bone to which it is applied.

As well as being useful for cutting between a prosthesis and a concave inner wall of a long bone, the second tool 21 may also be usable to cut circular bone samples, or in cranial surgery. Although a generally hemicylindrical blade 27 is probably optimal for arthroplasty revision work, blades comprising greater or lesser proportions of a hollow cylinder may be appropriate in other applications.

A third osteotomy tool 31, shown in FIG. 4, is a preferred variant of the first tool 1, shown in FIG. 1. As for the first tool 1, the third tool 31 comprises a connecting body 2 having a threaded spigot 3, by which the tool 31 may detachably be connected to a generator of ultrasonic vibrations. An elongate blade portion 4 extends from a distal end of the connecting body 2, generally coaxially aligned therewith.

The blade portion 4 comprises a proximal blade root 5 of generally rectangular cross-section, linked by a tapered portion 6 to a thin, elongate blade 37 with a generally rounded distal tip 8. As for the blade 7 of the first tool 1, this comprises a distal portion having two oppositely-facing lateral cutting edges 9, 10. A plurality of teeth 13 extend along each cutting edge 9,10 and the rounded tip 8 that joins them.

The blade 37 of the third tool 31 differs in cross-sectional profile from that of the first tool 1. Whereas the blade 7 has a rectangular cross-section, the blade 37 has a substantial bevelled region 32 extending longitudinally of the blade 37 adjacent each edge 33 thereof and around its distal tip 8. (A corresponding bevelled region 32 is provided on a reverse face of the blade 37 to that visible in FIG. 4).

Figure 5:
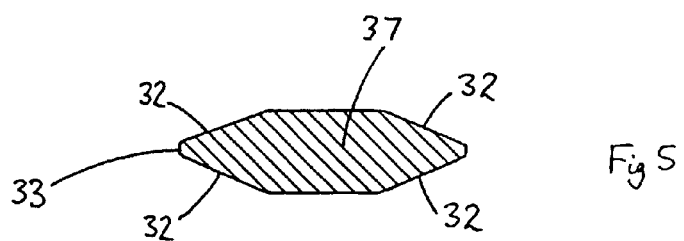
FIG. 5 is a cross-sectional elevation of a blade of the tool shown in FIG. 4, taken along the line V-V.

Thus, as shown more clearly in FIG. 5, the blade 37 has an octagonal cross-section. Respective bevelled regions 32 on each face of the blade 37 define a narrow edge 33 extending between them. It is preferable that the edge 33 is not actually sharpened, to reduce the likelihood of it cutting anything accidentally while the tool 31 is not ultrasonically activated.

Figure 6:
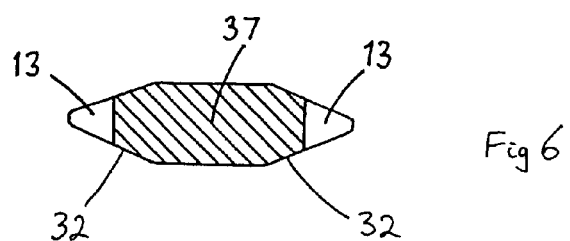
FIG. 6 is a cross-sectional elevation of a blade of the tool shown in FIG. 4, taken along the line VI-VI.

As shown in FIG. 6, the indentations between the teeth 13 of the blade 37 extend only partially across the bevelled regions 32. They are thus both triangular in plan view (see FIGS. 2 and 3) and generally triangular in profile.

The teeth 13 of the blade 7 of the first tool 1 have a substantially rectangular cross-section, and it is believed that the outer corners thereof may be prone to damage. It is probable that an activated tool 1 would at some point come into contact with a prosthesis being removed and the corners of the teeth 13 would tend to impact thereon. There would be a significant chance of these corners being knocked off, notched or chipped as a result. It is important to balance an ultrasonically-vibratable blade, and significant loss of material from the teeth 13 might require the whole blade 7 to be rebalanced or even disposed of. Also, if damage occurs at a region of the blade 7 that is under raised stress, fatigue fractures of the blade 7 might quickly follow, originating from the damage.

The blade 37 with bevelled regions 32 avoids such problems to a great extent. While a face of the blade 37 might contact the prosthesis in use, its teeth 13 (and particularly the narrow edge 33 forming the tips of the teeth 13) are set back from the face and less likely contact the prosthesis. Even if they did, the profile created means that such contacts would be more glancing and less liable to cause damage. Nevertheless, the tooth 13 profile of the blade 37 of the third tool 31 is just as effective as that of the first tool in cutting through cancellous bone.

A similar tapered profile may also be created around the cutting distal tip 28 of the second tool 21.

While the present disclosure has been illustrated with respect to several specific embodiments thereof, these embodiments should be considered as illustrative rather than limiting. Various modifications and additions may be made and will be apparent to those skilled in the art.

The invention claimed is:

1. A tool adapted to cut bone using ultrasonic vibrations, comprising:
   a connecting body;
   a blade root distally located from said connecting body;
   an elongated blade; and
   a tapering portion in between said blade root and said elongated blade,
   wherein the blade comprises a cutting section having first and second lateral cutting edges connected to a rounded distal cutting edge, the elongated blade having a plurality of triangular serrations disposed on the first and second lateral cutting edges and on the rounded distal cutting edge, the triangular serrations extending in a continuous array along the first lateral cutting edge around the distal cutting edge and along the second lateral cutting edge without the dispositions of the triangular serrations changing relative to the blade, wherein each of the triangular serrations defining a first cutting facet extending about orthogonally from the elongated blade, and a second angled facet extending obliquely from the elongated blade, wherein the tool is configured for connection to an ultrasonic vibration generator.

2. A tool as claimed in claim 1, wherein the ultrasonic vibration generator produces longitudinal mode ultrasonic vibrations directed substantially parallel to a longitudinal axis of the blade.

3. A tool as claimed in claim 1, wherein the blade is substantially planar.

4. A tool as claimed in claim 3, wherein the first and second lateral cutting edges are substantially parallel to the longitudinal axis of the blade.

5. A tool as claimed in claim 1, wherein the first lateral cutting edge is adapted to cut on a longitudinal pull stroke and the second lateral cutting edge is adapted to cut on a longitudinal push stroke.

6. A tool as claimed in claim 1, wherein each pair of neighboring triangular serrations of the plurality of triangular serrations is disposed in spaced relation to each other such that a first facet of one triangular serration of said pair is adjacent to a second facet of a next triangular serration of said pair.

7. A tool as claimed in claim 1, wherein the plurality of triangular serrations defines a continuous array of triangular serrations on the first lateral cutting edge, on the rounded distal cutting edge, and on the second lateral cutting edge of the blade.

8. A tool as claimed in claim 1, wherein said blade root has a rectangular cross-section.

9. A tool as claimed in claim 1, further comprising a threaded spigot connected to said connecting body, wherein said threaded spigot is detachably connected to said ultrasonic vibration generator.

\* \* \* \* \*